(12) United States Patent
Uehara et al.

(10) Patent No.: US 7,189,868 B2
(45) Date of Patent: Mar. 13, 2007

(54) CYCLIC SILOXANE COMPOUNDS AND MAKING METHOD

(75) Inventors: Katsuhiro Uehara, Joetsu (JP); Tohru Kubota, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/435,936

(22) Filed: May 18, 2006

(65) Prior Publication Data

US 2006/0264649 A1    Nov. 23, 2006

(30) Foreign Application Priority Data

May 19, 2005    (JP)    ............................. 2005-146308
Jun. 15, 2005    (JP)    ............................. 2005-174538

(51) Int. Cl.
    *C07F 7/04*    (2006.01)
(52) U.S. Cl. ...................... 556/460; 556/467
(58) Field of Classification Search ................ 556/460, 556/467
    See application file for complete search history.

(56) References Cited

U.S. PATENT DOCUMENTS

| 4,111,973 A | 9/1978 | Bluestein |
| 4,855,379 A | 8/1989 | Budnik et al. |
| 5,041,468 A | 8/1991 | Budnik et al. |
| 5,290,841 A | 3/1994 | Enami et al. |
| 6,037,486 A | 3/2000 | Razzano |

FOREIGN PATENT DOCUMENTS

| JP | 54-90120 A | 7/1979 |
| JP | 63-014787 A | 1/1988 |
| JP | 01-281135 A | 11/1989 |
| JP | 04-217690 A | 8/1992 |
| JP | 07-149902 A | 6/1995 |
| JP | 2000-169485 A | 6/2000 |
| JP | 2001-114835 A | 4/2001 |

OTHER PUBLICATIONS

O. Mukhbaniani et al., "Cyclic and linear organosiloxanes with norbornene-2-yl groups at silicon atom", Izvestiya Akademii Nauk Gruzii, Seriya Khimicheskaya, 2001, pp. 53-57, 27 (1-2).

Y. Fukukawa et al., "Synthesis of Fluorosilicone Having Highly Fluorinated Alkyl Side Chains Based on the Hydrosilylation of Fluorinated Olefins with Polyhydromethylsiloxane", Journal of Polymer Science : Part A: Polymer Chemistry, vol. 40, 2002, pp. 3120-3128.

*Primary Examiner*—J. Parsa
(74) *Attorney, Agent, or Firm*—Westerman, Hattori, Daniels & Adrian, LLP.

(57) ABSTRACT

Novel cyclic siloxane compounds have both an aliphatic unsaturation-containing organic group and fluorinated alkyl groups within the molecular structure. When used to form silicone fluids and rubbers, they are useful as a modifier for giving novel physical properties thereto and when used as polymerizable monomers, they are effective for improving the performance of polymers or forming polymers with novel physical properties.

10 Claims, 4 Drawing Sheets

CYCLIC SILOXANE COMPOUNDS AND MAKING METHOD

CROSS-REFERENCE TO RELATED APPLICATION

This non-provisional application claims priority under 35 U.S.C. §119(a) on Patent Application Nos. 2005-146308 and 2005-174538 filed in Japan on May 19, 2005 and Jun. 15, 2005, 10 respectively, the entire contents of which are hereby incorporated by reference.

1. Technical Field

This invention relates to novel cyclic siloxane compounds having both an aliphatic unsaturation-containing organic group and fluorinated alkyl groups within the molecular structure which are useful as a modifier for giving novel physical properties to silicone fluids and silicone rubbers and when used as polymerizable monomers, as a modifier for giving novel physical properties to various resins and polymer compositions; and a method for preparing the same.

2. Background Art

Several cyclic siloxane compounds having an aliphatic unsaturation-containing organic group are known in the art.

For example, U.S. Pat. No. 4,855,379 or JP-A 1-281135 describes the following compound as a raw material to modified silicone.

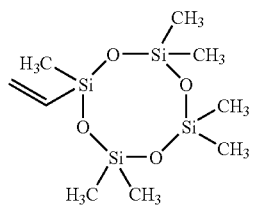

JP-A 7-149902 describes the following compound as a raw material to form an electron beam-curable silicone polymer composition.

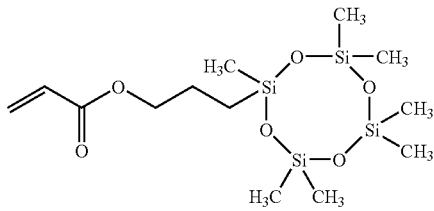

JP-A 2001-114835 describes the following compound as a component in a chemically amplified positive resist composition.

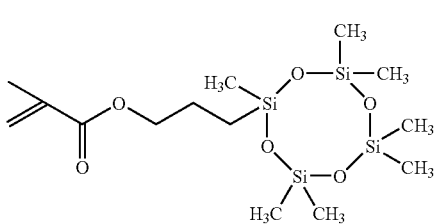

JP-A 4-217690 describes the following compound as a silane coupling agent, resin modifier or surface modifier.

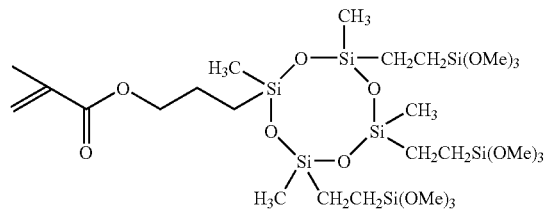

JP-A 63-14787 describes the following compound as a raw material to acrylic polymer or rubber.

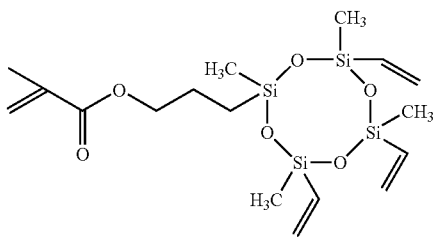

The following compound is described in O. Mukhbaniani et al., Izvestiya Akademii Nauk Gruzii, Seriya Khimicheskaya (2001), 27 (1–2), p 53–57.

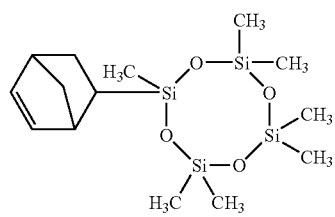

Also, several cyclic siloxane compounds having fluorinated alkyl groups are known in the art. For example, JP-A 2000-169485, JP-A 54-90120, and Silicone Handbook, K. Ito Ed., Nikkan Kogyo Shinbun, pp. 560–563 describe the following compounds which are useful as raw materials to form fluorinated silicone fluids and fluorinated silicone rubbers.

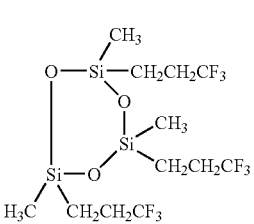

(3)

-continued

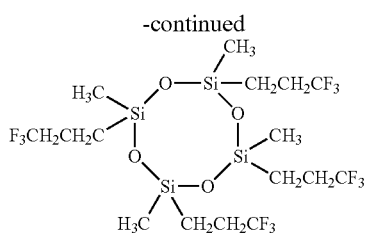

In particular, 1,3,5-tris(3',3',3'-trifluoropropyl)-1,3,5-hexamethylcyclotrisiloxane of the above formula (3) is useful in the above-mentioned application.

The cyclic siloxanes described above are used in many applications in a variety of fields by various means. For example, it is known to prepare high molecular weight silicone fluids or silicone rubbers by reacting cyclic siloxanes having various functional groups alone or with cyclic or linear siloxane compounds of other types in the presence of equilibration catalysts such as acids or alkalis. Various performances of the polymers are improved depending on the properties of functional group. Where cyclic siloxanes have unsaturation-containing organic groups, it is known to prepare polymers by polymerizing the unsaturated groups alone or with another unsaturation-containing organic compound through various measures. These polymers have a cyclic siloxane structure chemically firmly bonded to the backbone. Various performances of the polymers are improved depending on the properties of cyclic siloxane structure.

Nevertheless, prior to the present invention, cyclic siloxane compounds having both an unsaturation-containing organic group and fluorinated alkyl groups within the molecular structure are not known. It was thus impossible to further improve various performances of polymers or to further give novel performance.

DISCLOSURE OF THE INVENTION

An object of the present invention is to provide novel cyclic siloxane compounds having both an aliphatic unsaturation-containing organic group and fluorinated alkyl groups within the molecular structure and a method for preparing the same.

The inventors have found that a novel cyclic siloxane compound having both an aliphatic unsaturation-containing organic group and fluorinated alkyl groups within the molecular structure is obtained by reacting a dichlorosilane having an aliphatic unsaturation-containing organic group with a cyclic siloxane compound having fluorinated alkyl groups in the presence of a catalyst to synthesize a silane compound having chloro at both ends as an intermediate, then effecting hydrolysis of the compound.

In one aspect, the present Invention provides a cyclic siloxane compound having the general formula (1):

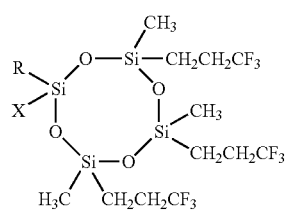

(1)

wherein X is an aliphatic unsaturation-containing organic group and R is a $C_1$–$C_6$ alkyl or phenyl.

In a preferred embodiment, X is a group having the formula:

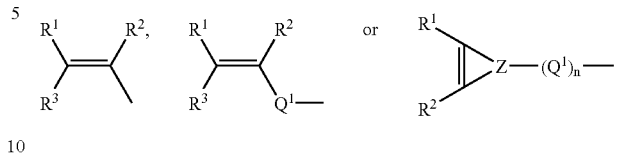

wherein $R^1$, $R^2$ and $R^3$ are each independently hydrogen, $C_1$–$C_6$ alkyl or phenyl, $Q^1$ is a divalent organic group, Z is a trivalent organic group and n is 0 or 1. Typically $Q^1$ is a linear, branched or cyclic alkylene group having 1 to 8 carbon atoms, or an alkylene group which may have a branch and in which at least one methylene unit of the main chain and/or the side chain of the alkylene group may be substituted with at least one substituent group selected from the group consisting of —O—, —CO—, —COO—, —OCO—, —OCOO—, —$C_6H_4$—, —O$C_6H_4$—, —$C_6H_4$O— and —S— and the main chain of the alkylene group has 1 to 8 carbon atoms. Also typically Z is a trivalent hydrocarbon group having 1 to 21 carbon atoms that forms a cyclic structure with the unsaturated bond to which $R^1$ and $R^2$ are attached, or a trivalent hydrocarbon group having 2 to 21 carbon atoms in which a methylene unit of the cyclic structure is substituted with at least one substituent group selected from the group consisting of —O—, —CO—, —COO—, —OCO—, —OCOO—, —$C_6H_4$—, —O$C_6H_4$—, —$C_6H_4$O— and —S—.

In one preferred embodiment, R in formula (1) is methyl and X has the formula:

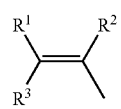

wherein $R^1$, $R^2$ and $R^3$ are each independently hydrogen or methyl.

In another preferred embodiment, R in formula (1) is methyl and X has the formula:

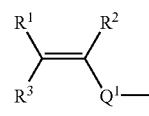

wherein $R^1$, $R^2$ and $R^3$ are each independently hydrogen or methyl, and $Q^1$ has the formula:

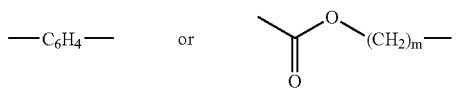

wherein m is 1 to 3.

In a further preferred embodiment, R in formula (1) is methyl and X has the formula:

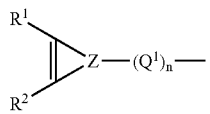

wherein $R^1$ and $R^2$ are each independently hydrogen or methyl, and $Z-(Q^1)_n-$ has the formula:

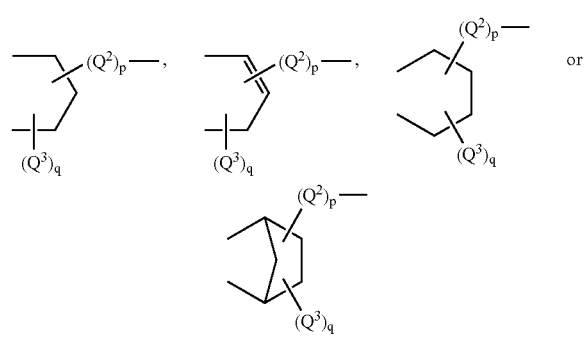

wherein $Q^2$ is $-(CH_2)_r-$ or a group in which a methylene unit of $-(CH_2)_r-$ is substituted with at least one substituent group selected from the group consisting of $-O-$, $-CO-$, $-COO-$, $-OCO-$, $-OCOO-$, $-C_6H_4-$, $-OC_6H_4-$, $-C_6H_4O-$ and $-S-$, $Q^3$ is a monovalent hydrocarbon group having 1 to 8 carbon atoms, p and q are independently 0 or 1, and r is an integer of 1 to 8.

The present invention is also directed to a method for preparing a cyclic siloxane compound having the general formula (1), comprising the steps of reacting a dichlorosilane compound bearing an aliphatic unsaturation-containing organic group and having the general formula (2) with a fluorinated cyclic siloxane compound having the general formula (3) in the presence of a catalyst, and reacting the resulting reaction mixture with water.

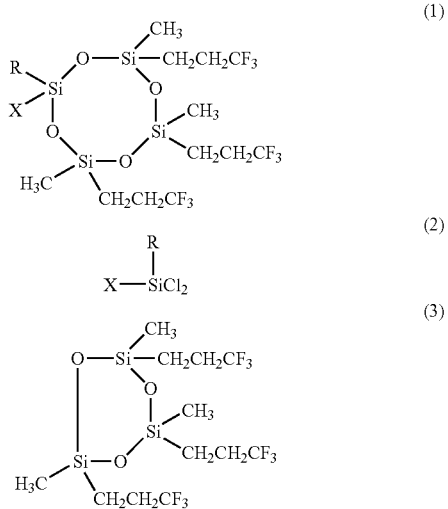

Herein X is an aliphatic unsaturation-containing organic group and R is a $C_1-C_6$ alkyl or phenyl.

The catalyst is typically selected from among aprotic polar solvents, quaternary ammonium salts, and quaternary phosphonium salts. More preferably the catalyst is an aprotic polar solvent selected from among dimethoxyethane, dimethylformamide, hexamethylphosphoric triamide, dimethyl sulfoxide, N-methylpyrrolidone, dimethylimidazolidinone, and acetonitrile.

BENEFITS OF THE INVENTION

The present invention offers novel cyclic siloxane compounds having both an aliphatic unsaturation-containing organic group and fluorinated alkyl groups within the molecular structure and a method for preparing the same. When the novel cyclic siloxane compounds are used as raw materials to form silicone fluids and silicone rubbers, they are useful modifiers for achieving further performance improvements or giving novel physical properties. When the novel cyclic siloxane compounds are used as polymerizable monomers, they are effective for improving the performance of the resulting polymers or forming polymers with novel physical properties. The method enables to produce the desired cyclic siloxane compounds in high yields and at high purity through simple steps under moderate conditions using commercially available inexpensive raw materials.

DESCRIPTION OF THE PREFERRED EMBODIMENTS

Figure 1:
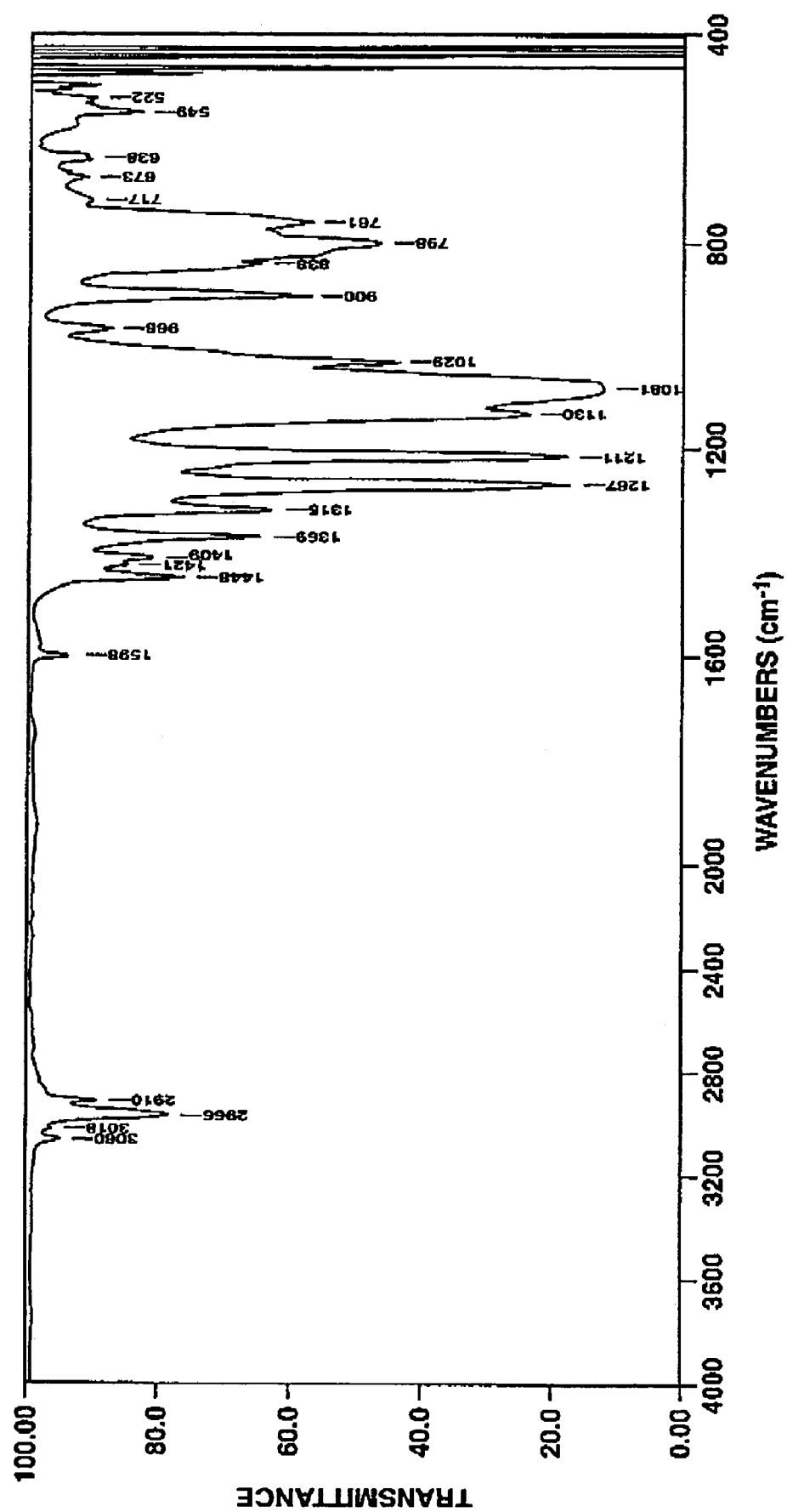
FIG. 1 is an IR spectral chart of the compound obtained in Example 1.

One embodiment of the invention provides novel cyclic siloxane compounds having the general formula (1):

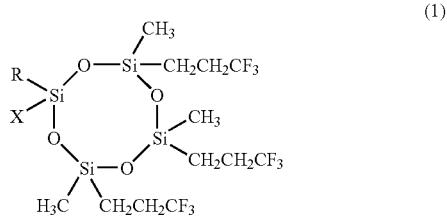

wherein X is an aliphatic unsaturation-containing organic group and R Is a $C_1-C_6$ alkyl or phenyl. In another embodiment, the cyclic siloxane compound having formula (1) is prepared by reacting a dichlorosilane compound bearing an aliphatic unsaturation-containing organic group, represented by the general formula (2):

(2)

wherein X is an aliphatic unsaturation-containing organic group and R is a $C_1$–$C_6$ alkyl or phenyl with a fluorinated alkyl-bearing cyclic siloxane compound represented by the general formula (3):

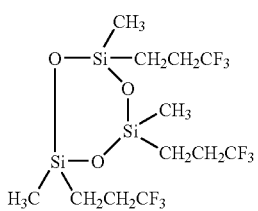
(3)

in the presence of a catalyst, and reacting the resulting reaction mixture with water.

The preparation method of the invention is described in detail. The preparation method forms the target compounds, i.e., novel cyclic siloxane compounds of formula (1) through a reaction route including two stages. The first stage is to react a dichlorosilane compound bearing an aliphatic unsaturation-containing organic group of formula (2) with a fluorinated alkyl-bearing cyclic siloxane compound of formula (3) in the presence of a catalyst, thereby opening the cyclic structure to form an intermediate, i.e., both end chloro-terminated silane compound having the general formula (4):

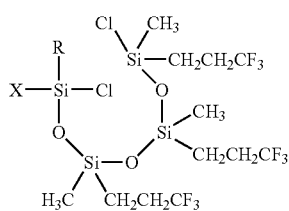
(4)

wherein X and R are as defined above. This step is illustrated by the reaction scheme I below and hereinafter, referred to as "ring-opening reaction."

Reaction scheme I:

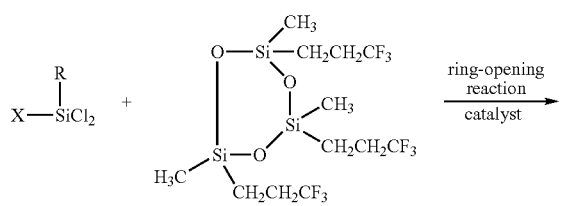

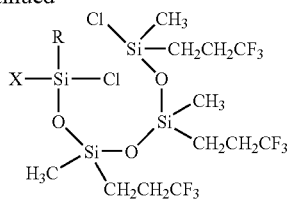

Herein, X and R are as defined above.

The second stage is to further react the both end chloro-terminated silane compound of formula (4) with water, thereby causing ring-closure to the molecular structure to form the target substance, i.e., novel cyclic siloxane compound of formula (1). This step is illustrated by the reaction scheme II below and hereinafter, referred to as "hydrolysis reaction."

Reaction scheme II:

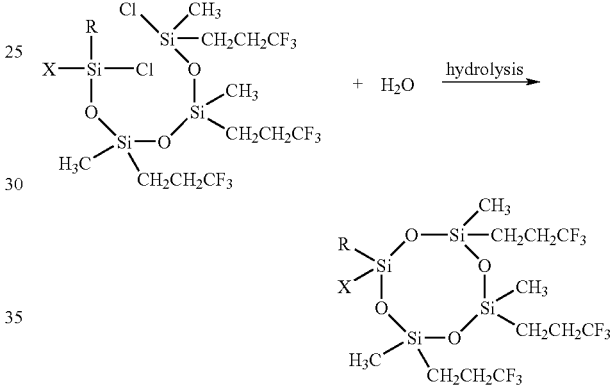

Herein, X and R are as defined above.

Preferably, X is an organic group having the formula:

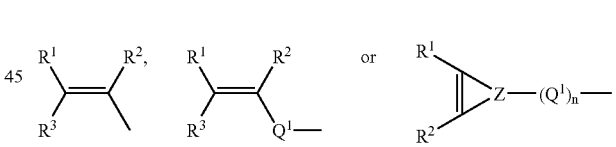

wherein $R^1$, $R^2$ and $R^3$ which may be the same or different are selected from hydrogen, $C_1$–$C_6$ alkyl and phenyl, $Q^1$ is a divalent organic group, Z is a trivalent organic group and n is 0 or 1.

The divalent organic group represented by $Q^1$ includes a linear, branched or cyclic alkylene group having 1 to 8 carbon atoms, or an alkylene group which may have a branch (i.e., a linear or branched alkylene group) and in which a methylene unit of the main chain of the linear alkylene group or the main chain and/or the side chain of the branched alkylene group may be substituted with at least one substituent group selected from among —O—, —CO—, —COO—, —OCO—, —OCOO—, —$C_6H_4$—, —O$C_6H_4$—, —$C_6H_4$O— and —S—. In the alkylene group which may have a branch, the main chain preferably has 1 to 8 carbon atoms. The side chain may be linear, branched or cyclic and may preferably have 1 to 20 carbon atoms, more preferably 1 to 10 carbon atoms.

The trivalent organic groups represented by Z include trivalent hydrocarbon groups having 1 to 21 carbon atoms that forms a cyclic structure with the unsaturated bond to which $R^1$ and $R^2$ are attached, and trivalent hydrocarbon groups having 2 to 21 carbon atoms forming the above cyclic structure in which a methylene unit of the cyclic structure is substituted with at least one substituent group selected from among —O—, —CO—, —COO—, —OCO—, —OCOO—, —C$_6$H$_4$—, —OC$_6$H$_4$—, —C$_6$H$_4$O— and —S—.

Exemplary of the $C_1$–$C_6$ alkyl are methyl, ethyl, propyl, isopropyl, butyl, isobutyl, tert-butyl, pentyl, isopentyl, and hexyl. Examples of the $C_1$–$C_8$ alkylene groups include methylene, ethylene, propylene, butylene, pentylene, hexylene, isobutylene, isopentylene, ethylhexylene, cyclopentylene and cyclohexylene.

Illustrative, non-limiting examples of the portion that forms a cyclic structure with the unsaturated bond to which $R^1$ and $R^2$ are attached, included in the hydrocarbon group represented by the formula:

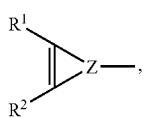

are given below.

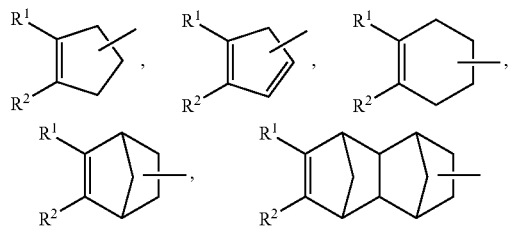

In a preferred embodiment of the cyclic siloxane compound, R in formula (1) is methyl and X is a group having the formula:

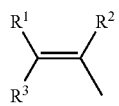

wherein $R^1$, $R^2$ and $R^3$ are each independently hydrogen or methyl; in another preferred embodiment, R in formula (1) is methyl and X is a group having the formula:

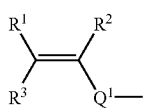

wherein $R^1$, $R^2$ and $R^3$ are each independently hydrogen or methyl, and $Q^1$ has the formula:

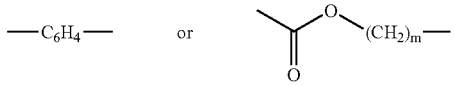

wherein m is 1 to 3; in a further preferred embodiment, R in formula (1) is methyl and X is a group having the formula;

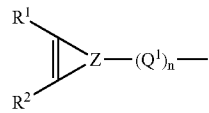

wherein $R^1$ and $R^2$ are each independently hydrogen or methyl, and Z—$(Q^1)_n$— has the formula;

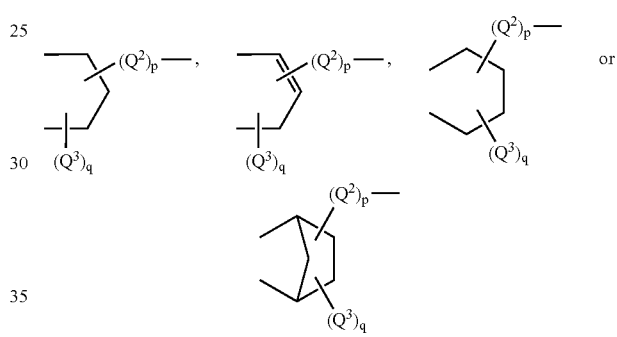

wherein $Q^2$ is —(CH$_2$)— or a group in which a methylene unit of —(CH$_2$)$_r$— is substituted with at least one substituent group selected from the group consisting of —O—, —CO—, —COO—, —OCO—, —OCOO—, —C$_6$H$_4$—, —OC$_6$H$_4$—, —C$_6$H$_4$O— and —S—, $Q^3$ is a monovalent hydrocarbon group (such as an alkyl group) having preferably 1 to 8, more preferably 1 to 3 carbon atoms, p and q are independently 0 or 1, and r is an integer of 1 to 8, preferably 1 to 3.

Illustrative, non-limiting examples of X are given below.

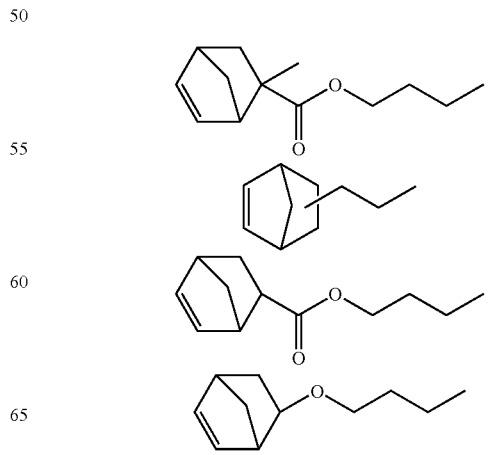

-continued

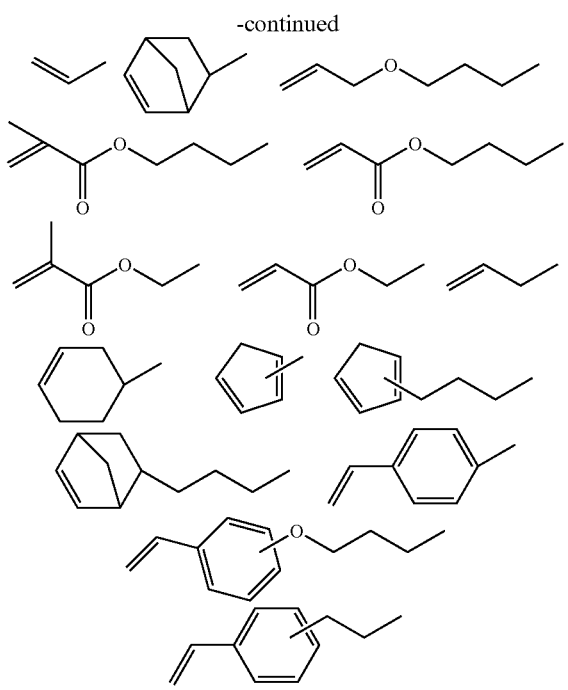

The method of the invention starts with a dichlorosilane compound bearing an aliphatic unsaturation-containing organic group, represented by the general formula (2):

(2)

wherein X and R are as defined above.

The dichlorosilane compounds bearing an aliphatic unsaturation-containing organic group of formula (2) are well-known in the art and available in plenty on an industrial scale. Since a number of variant methods are known for the preparation of dichlorosilane compounds of formula (2), the preparation is not limited to a single method in one exemplary method, a dichlorosilane compound of formula (2) can be synthesized through hydrosilylation reaction of a silicon-bonded hydrogen-containing dichlorosilane compound having the general formula (5):

(5)

wherein R is as defined above with another reactant, compound having an aliphatic unsaturation-containing organic group and an allyl or vinyl group in the presence of a hydrosilylation catalyst containing a transition metal such as platinum, rhodium, iridium or palladium.

Examples of the compound having an aliphatic unsaturation-containing organic group and an allyl or vinyl group are given below.

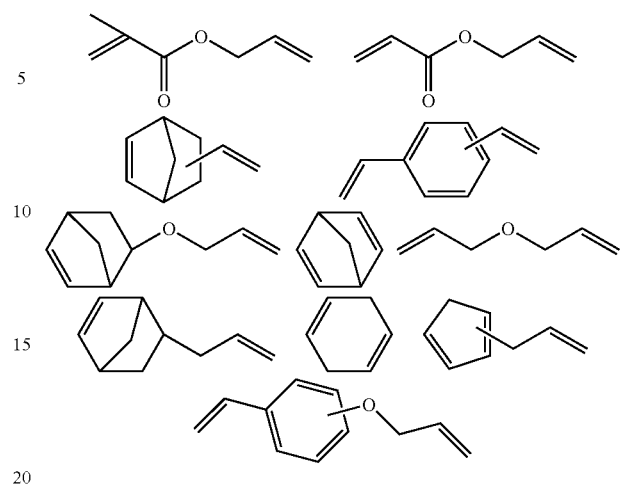

Alternatively, a vinyl-containing silicon compound can be synthesized through hydrosilylation reaction of an acetylene compound with a silicon-bonded hydrogen-containing dichlorosilane compound in the presence of a platinum catalyst. Other well-known methods for synthesizing an aliphatic unsaturation-containing dichlorosilane compound into a silicon atom include Grignard reaction of a Grignard reagent having an aliphatic unsaturation-containing organic group with a chlorosilane compound; desalting reaction of a haloalkyl group-containing silane compound with an alkali metal salt having an aliphatic unsaturation-containing organic group; Diels-Alder addition reaction of a chlorosilane compound having an aliphatic unsaturation-containing organic group with a conjugated diene compound; and the like.

It is understood that R is most preferably methyl because corresponding compounds are available in plenty and at low cost on an industrial scale.

Illustrative examples of the compounds of formula (2) are given below although the invention is not limited thereto.

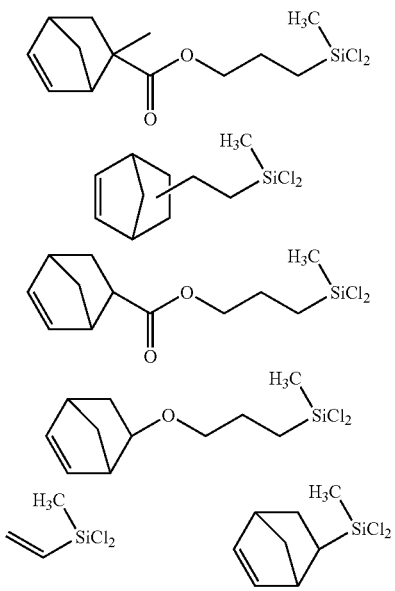

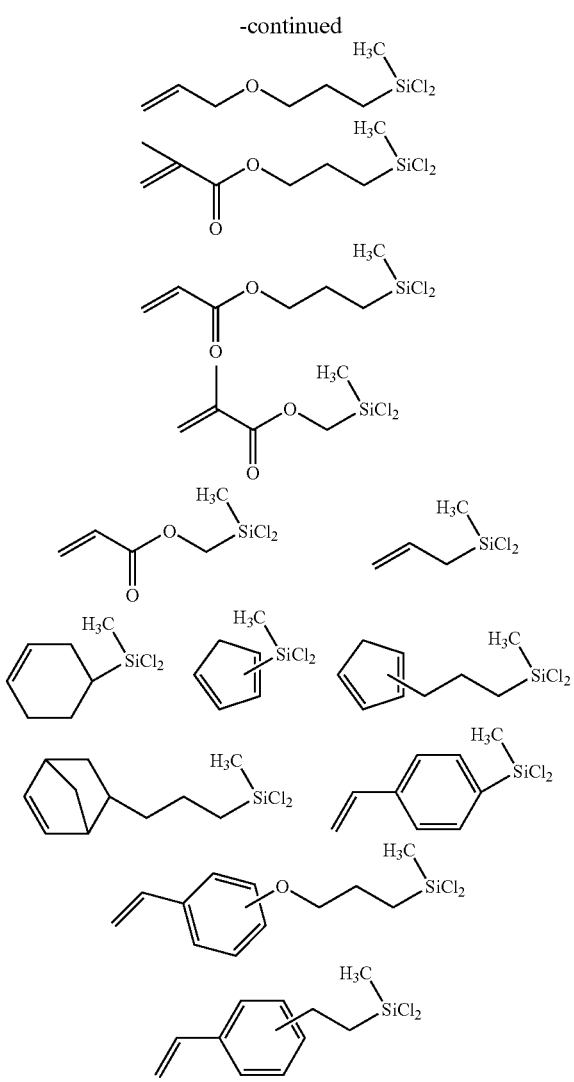

The other reactant, fluorinated alkyl-bearing cyclic siloxane compound of formula (3):

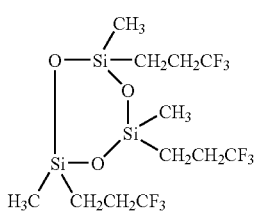

(3)

is 1,3,5-tris(3',3',3'-trifluoropropyl)-1,3,5-trimethylcyclotrisiloxane.

This compound is also available in plenty and at low cost on an industrial scale. As described in Y. Furukawa, M. Kotera, Journal of Polymer Science: Part A: Polymer Chemistry, Vol. 40, 3120–3128 (2002), for example, the compound is prepared by effecting hydrosilylation reaction of methyldichlorosilane with trifluoropropane in the presence of a platinum catalyst, usually in a closed pressure vessel, to synthesize 3,3,3-trifluoropropylmethyldichlorosilane. This is then hydrolyzed to synthesize a mixture of cyclic and linear structure siloxanes consisting of divalent 3,3,3-trifluoropropylmethylsiloxane units. The mixture is then held in the presence of an alkali catalyst under vacuum reflux conditions to induce equilibration of siloxane linkages. Finally, the compound of formula (3) is withdrawn from the system as a fraction that refluxes at the lowest boiling point. This process is generally known as cracking reaction. See JP-A 2000-169485, page 2, [0002]–[0004] and JP-A 54-90120, page 154. In this way, the compound of formula (3) is obtained in a large quantity and at a high purity.

The reaction conditions involved in the ring-opening reaction of the first stage are described in detail.

The ring-opening reaction of the first stage is to react a dichlorosilane compound bearing an aliphatic unsaturation-containing organic group of formula (2) with a fluorinated alkyl-bearing cyclic siloxane compound of formula (3) in the presence of a catalyst, thereby forming an intermediate, i.e., both end chloro-terminated silane compound of formula (4), as illustrated by the reaction scheme I below.

Reaction scheme I:

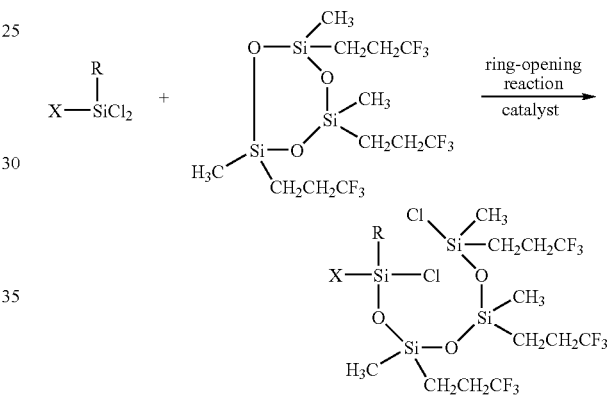

Herein, X and R are as defined above.

In the ring-opening reaction of the first stage, the molar ratio of the compound of formula (2) to the compound of formula (3) is not particularly limited. A molar ratio in the range of 0.8–1.2:1 is preferred. If the molar ratio is less than 0.8 or more than 1.2, one reactant which is present in excess is left unreacted in a larger proportion, which may be uneconomical in some cases or produce in some other cases impurities that interfere with purification of the target compound.

Examples of the catalyst used in the ring-opening reaction include aprotic polar solvents such as dimethoxyethane, dimethylformamide, hexamethylphosphoric triamide, dimethyl sulfoxide, N-methylpyrrolidone, dimethylimidazolidinone, and acetonitrile; quaternary ammonium salts such as tetrabutylammonium bromide, tetrabutylammonium chloride, tetrapropylammonium bromide and trioctylmethylammonium chloride; and quaternary phosphonium salts such as tetrabutylphosphonium bromide, tetrabutylphosphonium chloride and triphenylmethylphosphonium bromide.

The catalyst is preferably added in an amount of 0.001 to 200% by weight, more preferably 0.1 to 50% by weight based on the weight of the compound of formula (2). Less than 0.001 wt % of the catalyst may be too small to exert catalysis whereas more than 200 wt % may be economically disadvantageous. In this range, relatively large amounts of the catalyst are based on the assumption that the catalyst is used as a reaction medium (solvent) as well.

For the ring-opening reaction, the reaction temperature is not particularly limited although an appropriate temperature is in the range of 0 to 150° C., more preferably in the range of 3 to 100° C. A reaction temperature higher than 150° C. may be economically disadvantageous in some cases and produce in some other cases by-products that invite a reduced yield. A reaction temperature lower than 0° C. may slow down the reaction rate below the necessity.

For the ring-opening reaction, the method and order of mixing the reactants are not particularly limited. In possible alternatives, the compound of formula (2), the compound of formula (3) and the catalyst may be mixed altogether; the catalyst may be added dropwise to a mixture of the compound of formula (2) and the compound of formula (3); the compound of formula (2) or (3) may be added dropwise to a mixture of the compound of formula (3) or (2) and the catalyst; a mixture of the compound of formula (2) or (3) and the catalyst may be added dropwise to the compound of formula (3) or (2); the compound of formula (2) and the compound of formula (3) may be individually or combinedly added dropwise to the catalyst or a mixture of the catalyst and a solvent.

For the ring-opening reaction, a reaction solvent is essentially not requisite, but may be used if necessary for some purposes, for example, for increasing the volume of the reaction system for more effective agitation. Suitable solvents include aromatic hydrocarbons such as toluene, xylene, ethylbenzene, mesitylene, and decalin; aliphatic hydrocarbons such as hexane, isooctane, octane, decane, undecane, dodecane, tetradecane, hexadecane, and paraffin; ethers such as dibutyl ether, ethylene glycol dimethyl ether and dipropyl ether: siloxanes such as hexamethyldisiloxane and dimethylsilicone oil; and the above-described aprotic polar solvents, which may be used alone or in admixture. It is understood that the use of alcohols, amines and other solvents of the type capable of reacting with the chlorosilane of formula (2) should be avoided.

For the ring-opening reaction, the pressure may be either atmospheric or increased, with no particular limit being imposed. Most often, atmospheric pressure is sufficient.

For the ring-opening reaction, the atmosphere of the reaction system is not particularly limited. Since the compounds involved are flammable, it is generally desired from the fire-proofing aspect to use an inert gas atmosphere. Typical of the inert gas are nitrogen and argon.

The time of the ring-opening reaction is usually 0.1 to 100 hours, preferably 1 to 50 hours. Within less than 0.1 hour, the reaction may be incomplete to a certain extent and in some cases, an attempt of performing rapid reaction within a short time may invite a rapid rise of the system temperature due to the heat of reaction, causing hazards. More than 100 hours may be economically disadvantageous.

The reaction conditions involved in the hydrolysis reaction of the second stage are described in detail.

The hydrolysis reaction of the second stage is to further react the both end chloro-terminated silane compound of formula (4), which is the product of "ring-opening reaction" of reaction scheme I, with water, thereby effecting hydrolytic condensation between chloro groups at opposite ends for causing ring-closure to the molecular structure to form the target substance. i.e., novel cyclic siloxane compound of formula (1), as illustrated by the reaction scheme II below.

Reaction scheme II:

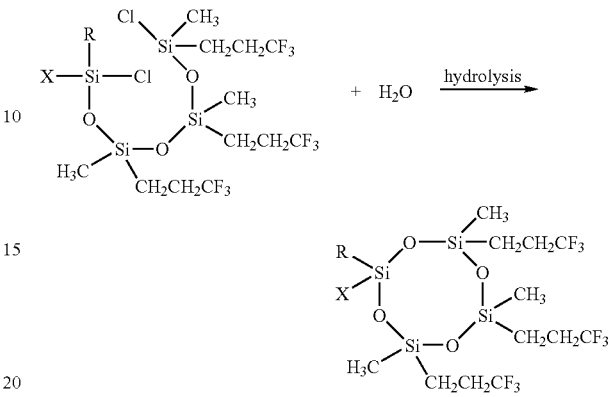

Herein, X and R are as defined above.

In the hydrolysis reaction of the second stage, the molar ratio of water to the chloro-terminated silane compound of formula (4) is not particularly limited. A molar ratio in the range of 1–1000:1 is preferred, with a molar ratio of 2–100:1 being more preferred. A molar ratio of less than 1 means the condition that water is stoichiometrically short so that some silane compound is left unreacted. A molar ratio of more than 1000 may be economically disadvantageous.

For the hydrolysis, the reaction temperature is not particularly limited although an appropriate temperature is in the range of 0 to 100° C., more preferably in the range of 3 to 50° C. A reaction temperature higher than 100° C. may cause water to boil, giving rise to a bumping phenomenon or the like, or produce impurities. A reaction temperature below 0° C. may cause water to freeze, interfering with agitation, or slow down the reaction rate below the necessity.

For the hydrolysis, the method of mixing the reactants is not particularly limited. Water may be added dropwise to the reaction mixture from the "ring-opening reaction" of the first stage containing the chloro-terminated silane compound of formula (4). Inversely, the reaction mixture may be added dropwise to water.

For the hydrolysis, an organic solvent may be used if necessary. The organic solvent may be added prior to or subsequent to the reaction. Suitable solvents include aromatic hydrocarbons such as toluene, xylene, ethylbenzene, mesitylene and decalin; aliphatic hydrocarbons such as hexane, isooctane, octane, decane, undecane, dodecane, tetradecane, hexadecane, and paraffin; ethers such as dibutyl ether, dipropyl ether, ethylene glycol dimethyl ether and tetrahydrofuran; siloxanes such as hexamethyldisiloxane and dimethylsilicone oil; ketones such as acetone, methyl ethyl ketone and methyl isobutyl ketone; esters such as ethyl acetate; and the above-described aprotic polar solvents, which may be used alone or in admixture.

Subsequent to the hydrolysis step, the organic layer may be washed with water by any well-known means. The organic layer is then subjected to distillation for removing the solvent. Prior to distillation, the residual water after water washing may be removed using commercially available desiccants such as $Na_2SO_4$ and $CaCl_2$. Without a particular water removal step, the organic layer may be subjected to is distillation whereby water is distilled off together with the solvent.

For the hydrolysis, the pressure may be either atmospheric or increased, with no particular limit being imposed. Most often, atmospheric pressure is sufficient.

For the hydrolysis, the atmosphere of the reaction system is not particularly limited. Since flammable compounds are involved, it is generally desired from the fire-proofing aspect to use an inert gas atmosphere. Typical of the inert gas are nitrogen and argon.

The reaction time for hydrolysis is usually 0.1 to 100 hours, preferably 1 to 50 hours. If the reaction time is less than 0.1 hour, the reaction may be incomplete to a certain extent and in some cases. More than 100 hours may be economically disadvantageous.

The preparation method described above yields the target substances, i.e., cyclic siloxane compounds having formula (1):

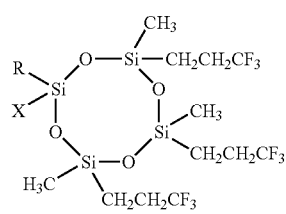

(1)

wherein X is an aliphatic unsaturation-containing organic group, preferably a group having the formula:

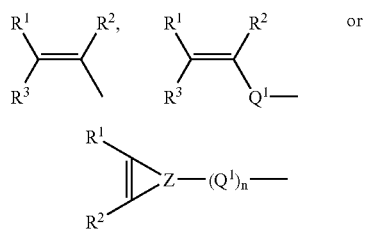

(wherein $R^1$, $R^2$, $R^3$, $Q^1$, Z and n are as defined above), and R is a $C_1$–$C_6$ alkyl group or phenyl group.

Illustrative examples of the cyclic siloxane compounds having both an aliphatic unsaturation-containing organic group and fluorinated alkyl groups within the molecular structure, as represented by formula (1), are given below although the invention is not limited thereto.

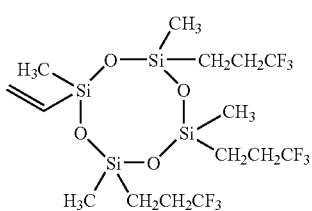

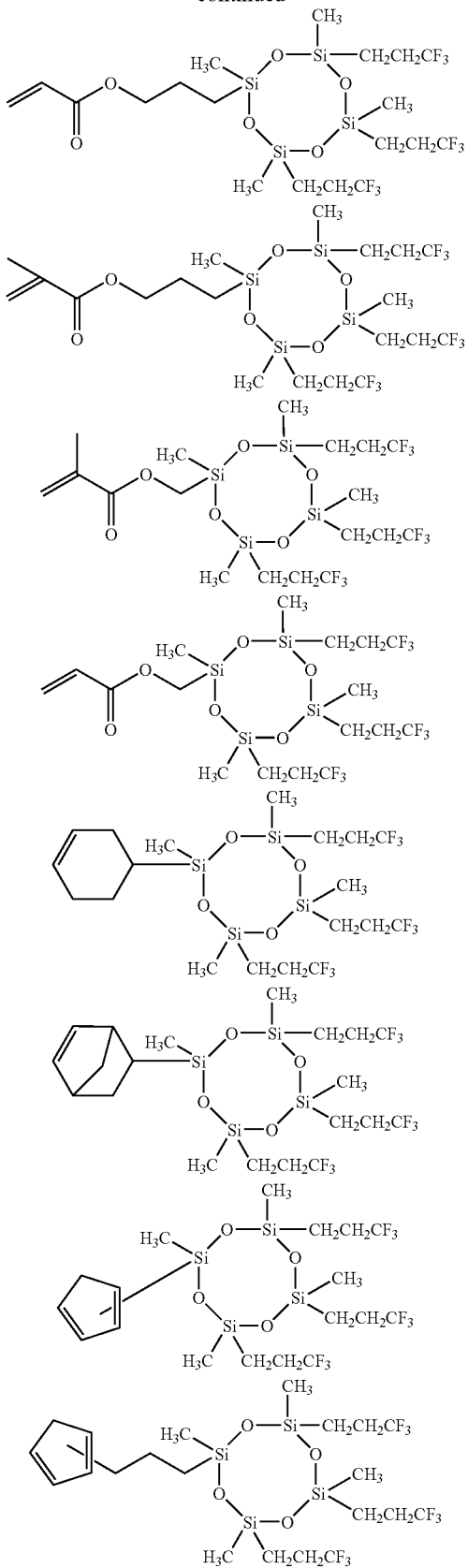

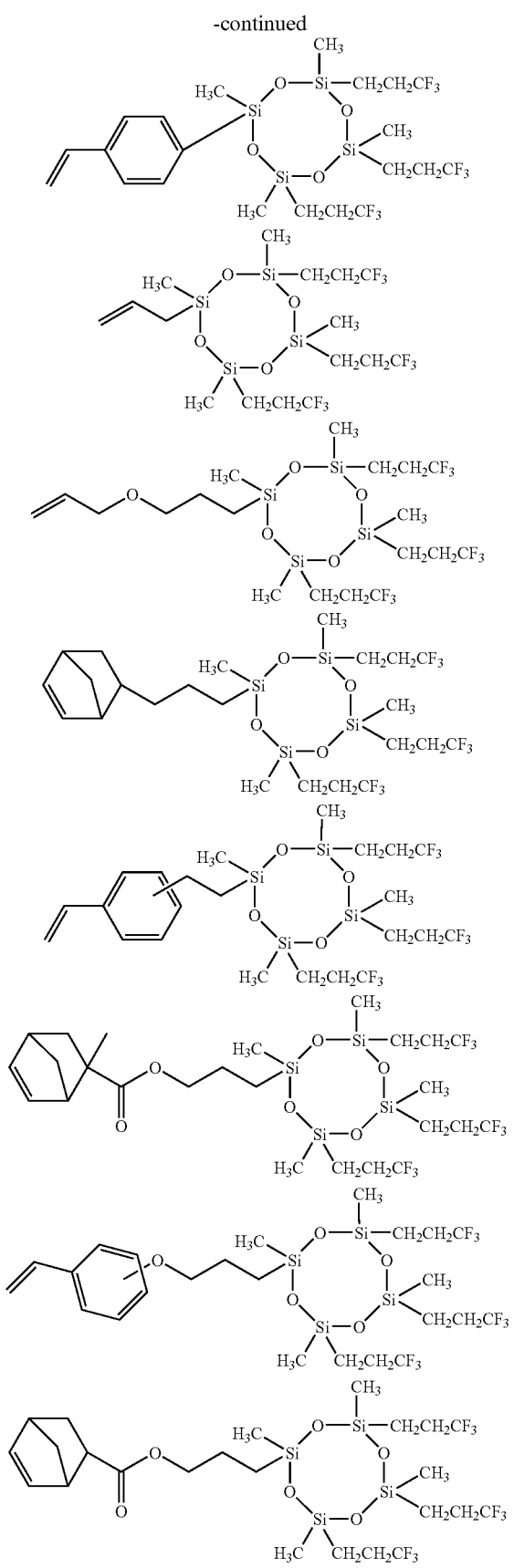

The cyclic siloxane compound of the invention may be isolated in a purer form through distillation of the reaction mixture. If the reaction mixture contains a solvent having a lower boiling point than the cyclic siloxane compound, the solvent is first distilled but of the system under predetermined distillation conditions, following which the reaction mixture is subjected to standard distillation under a reduced pressure of preferably less than or equal to 13 kPa, more preferably less than or equal to 7 kPa.

In the steps of ring-opening reaction, hydrolysis, and optional water washing and distillation, there can occur a phenomenon that the reaction mixture will thicken or gel due to self-polymerization reaction of aliphatic unsaturation-containing organic groups. The yield of the target substance is reduced by such a phenomenon. Any well-known polymerization inhibitor may be added in any step in order to prevent such a phenomenon Suitable polymerization inhibitors include phenolic compounds such as hydroquinone and hydroquinone monomethyl ether: hindered phenols such as 4-methyl-2,6-di-tert-butylphenol, 2,2'-methylenebis(4-methyl-6-tert-butylphenol), 2,2'-methylenebis(4-ethyl-6-tert-butylphenol), 4,4'-butylidenebis(6-tert-butyl-m-cresol), 1,3,5-trimethyl-2,4,6-tris(3,5-di-tert-butyl-4-hydroxybenzyl)benzene, tris(3,5-di-tert-butyl-4-hydroxybenzyl)isocyanurate, 2,2-thio-diethylene-bis[3-(3,5-di-tert-butyl-4-hydroxyphenyl)propionate], and 2,2'-methylenebis(4-methyl-6-tert-butylphenol)monoacrylate; copper compounds such as cuprous chloride, cupric chloride, cuprous oxide, cupric oxide, copper sulfate and copper dimethyldithiocarbamate; sulfur-containing compounds such as phenothiazine; nitrogen-containing compounds such as octylated diphenylamine and p-phenylenediamine; phosphorus-containing compounds such as triphenyl phosphate; and aliphatic conjugated unsaturation-containing compounds such as tung oil, dehydrated castor oil and conjugated linoleic oil.

The polymerization inhibitors may be used alone or in admixture of two or more. The amount of polymerization inhibitor added is not particularly limited although it is preferred to use the polymerization inhibitor in an amount of 0.01 to 10% by weight, more preferably 0.1 to 1% by weight based on the weight of the compound of formula (1) in the reaction mixture. Less than 0.01 wt % of the inhibitor may provide little stabilizing effect whereas more than 10 wt % may be economically disadvantageous.

The cyclic siloxane compounds having both an aliphatic unsaturation-containing organic group and fluorinated alkyl groups within the molecular structure, as prepared by the method of the invention, are commercially very useful as a modifier for giving novel physical properties to silicone resins and silicone fluids and when used as polymerizable monomers, as a modifier for various polymers. For example, when the compound of the invention alone or in combination with another cyclic or linear polysiloxane is subjected to equilibration reaction in the presence of an acid or alkali catalyst, a silicone fluid or rubber in which siloxane units having both an aliphatic unsaturation-containing organic group and fluorinated alkyl groups are incorporated as blocks in the structure is produced, offering improvements in various properties. Also, when the compound of the invention alone or in combination with another compound having an aliphatic unsaturation-containing organic group is polymerized by any well-known polymerization method, a polymer in which cyclic siloxane structures having fluorinated alkyl groups are attached to the polymer backbone as pendants is produced. This polymer is further improved in or newly provided with the properties associated respectively with fluorine atoms and siloxane, for example, water repellency, oil repellency, weather resistance, solvent resistance, chemical resistance, lubricity and texture.

EXAMPLE

Examples of the invention are given below by way of illustration and not by way of limitation.

Example 1

Synthesis of 1-vinyl-3,5,7-tris(3',3',3'-trifluoropropyl)-1,3,5,7-tetramethylcyclotetrasiloxane A four-necked flask equipped with a reflux condenser, stirrer and thermometer was thoroughly purged with nitrogen and charged with 140.6 g (0.3 mol) of 1,3,5-tris(3',3',3'-trifluoropropyl)-1,3,5-hexamethylcyclotrisiloxane which had been melted by heating the solid at 40–50° C. Then 42.3 g (0.3 mol) of vinylmethyldichlorosilane was fed to the flask. While allowing to cool and stirring, 0.3 g (0.0015 mol) of hexamethylphosphoric triamide (HMPA) was added dropwise to the mixture, which was controlled to a temperature around 50° C. and matured at the temperature for 2 hours. An analysis of the contents for composition by gas chromatography proved the completion of ring-opening reaction. The yield of the synthetic intermediate, both end chloro-terminated silane compound was about 91% as measured by GC.

Next, another four-necked flask equipped with a reflux condenser, stirrer and thermometer was thoroughly purged with nitrogen and charged with 162 g of water. While cooling with ice and stirring, the ring-opening reaction liquid was added dropwise over 1 hour to the water below 10° C. After the completion of dropwise addition, the mixture was matured for 30 minutes, after which the completion of hydrolysis reaction was confirmed. Then, 180 g of isooctane was fed to the reactor and the reaction mixture was washed with water by conventional means. After the water washing, the upper or organic layer was concentrated by removing isooctane under reduced pressure. By distillation under reduced pressure, 114 g of a liquid fraction having a boiling point of 101–105° C. at 0.1–0.2 kPa was collected. The fraction collected had a purity of 99% (a mixture of several structural isomers). Its quantity corresponded to a yield of 68% relative to the vinylmethyldichlorosilane.

The fraction was analyzed by infrared (IR) absorption spectroscopy, gas mass spectroscopy and proton nuclear magnetic resonance (NMR) spectroscopy. The results are shown below. With the data, the fraction was identified to be 1-vinyl-63,5,7-tris(3',3',3'-trifluoropropyl)-1,3,5,7-tetramethylcyclotetrasiloxane.

IR Spectra FIG. 1 Gas mass spectra molecular weight; 554 77: $CF_2=CH_2—CH_2^+$ 555: $(M+H)^+$ (isobutane-based CI) NMR (proton, $CDCl_3$ solvent)

Example 2

Synthesis of 1-(3'-methacryloxypropyl)-3,5,7-tris(3",3",3"-trifluoropropyl)-1,3,5,7-tetramethylcyclotetrasiloxane A four-necked flask equipped with a reflux condenser, stirrer and thermometer was thoroughly purged with nitrogen and charged with 117.1 g (0.25 mol) of 1,3,5-tris(3',3',3'-trifluoropropyl)-1,3,5-hexamethylcyclotrisiloxane and 60.3 g (0.25 mol) of 3-methacryloxypropylmethyldichlorosilane. While allowing to cool and stirring, 0.2 g (0–001 mol) of hexamethylphosphoric triamide (HMPA) was added dropwise to the mixture, which was controlled to a temperature around 50° C. and matured at the temperature for 3 hours. An analysis of the contents for composition by gas chromatography proved the completion of ring-opening reaction. The yield of the synthetic intermediate, both end chloro-terminated silane compound was about 84% as measured by GC.

Next, another four-necked flask equipped with a reflux condenser, stirrer and thermometer was thoroughly purged with nitrogen and charged with 136 g of water. While cooling with ice and stirring, the ring-opening reaction liquid was added dropwise over 4 hours to the water below 10° C. After the completion of dropwise addition, the mixture was matured for 1 hour, after which the completion of hydrolysis reaction was confirmed. Then, 184 g of isooctane was fed to the reactor and the reaction mixture was washed with water by conventional means. After the water washing, 0.48 g of copper-dimethyldithiocarbamate and 0–48 g of 1,3,5-trimethyl-2,4,6-tris(3,5-di-tert-butyl-4-hydroxybenzyl)benzene as the polymerization inhibitor was added to the upper or organic layer, which was concentrated by removing isooctane under reduced pressure. By distillation under reduced pressure, 106 g of a liquid fraction having a boiling point of 148–163° C. at 0.1–0.2 kPa was collected. The fraction collected had a purity of 99% (a mixture of several structural isomers). Its quantity corresponded to a yield of 64% relative to the 3-methacryloxypropylmethyldichlorosilane.

The fraction was analyzed by IR spectroscopy, gas mass spectroscopy and proton-NMR. The results are shown below. With the data, the fraction was identified to be 1-(3'-methacryloxypropyl)-3,5,7-tris(3",3",3"-trifluoropropyl)-1,3,5,7-tetramethylcyclotetrasiloxane.

Figure 2:
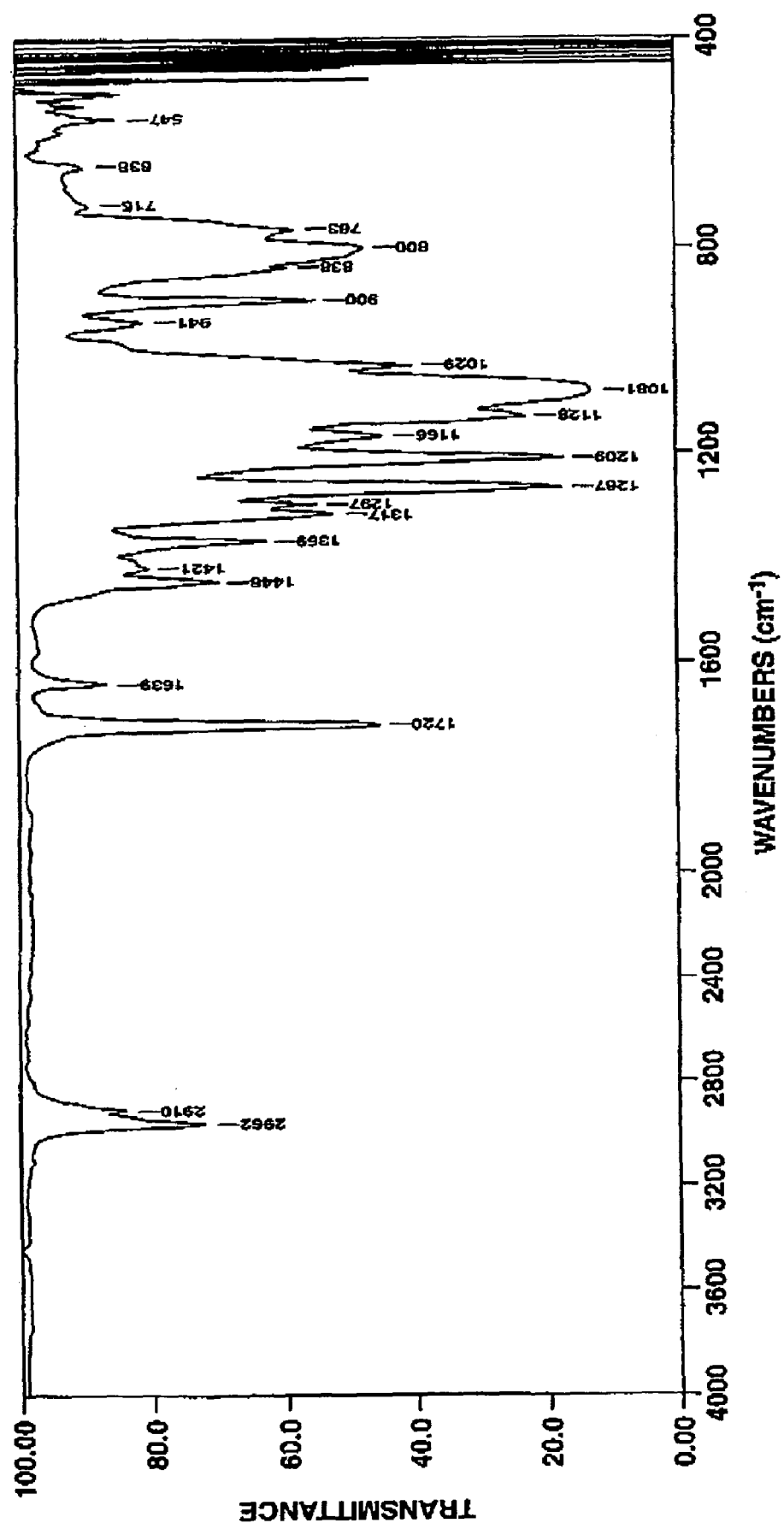
FIG. 2 is an IR spectral chart of the compound obtained in Example 2.

IR Spectra FIG. 2 Gas Mass Spectra molecular weight: 654 639: $(M—CH_3)^+$ 69: $CO—C(CH_3)=CH_2^+$ 77: $CF_2=CH_2—CH_2^+$ 41: $CH_2=CH—CH_2^+$ NMR (proton, $CDCl_3$ solvent)

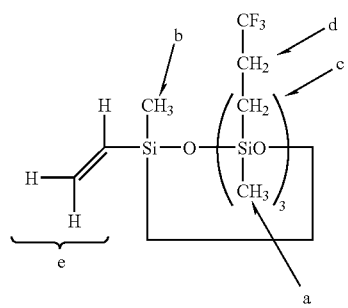

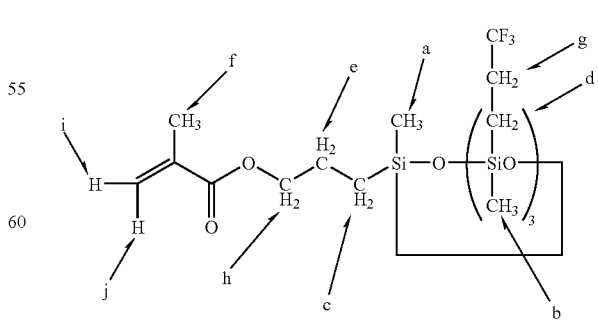

Letters "a" to "e" each denote a proton. NMR spectra: ppm (δ) (in $CDCl_3$) a: 0.16–0.17, d, 9H b: 0.20, s, 3H c: 0.74–0.84, m, 6H d: 1.96–2.16, m, 6H e: 5.74–6.10, m, 3H Letters "a" to "j" each denote a proton. NMR Spectra: ppm (δ) (in $CDCl_3$) a: 0.14, s, 3H b: 0.16, s, 9H c: 0.56–0.65, qui, 2H d: 0.73–0.83, qui, 6H e: 1.65–1.77, m, 2H f: 1.94, s, 3H g: 1.96–2.15, m, 6H h: 4.06–4.15, t, 2H i: 5.55, m, 1H j: 6.10, m, 1H Example 3

Synthesis of 1-norbornenyl-3,5,7-tris(3',3',3'-trifluoropropyl)-1,3,5,7-tetramethylcyclotetrasiloxane A four-necked flask equipped with a reflux condenser, stirrer and thermometer was thoroughly purged with nitrogen and charged with 117.1 g (0.25 mol) of 1,3,5-tris(3',3',3'-trifluoropropyl)-1,3,5-hexamethylcyclotrisiloxane and 51.8 g (0.25 mol) of norbornenylmethyldichlorosilane. While allowing to cool and stirring, 0.2 g (0.0013 mol) of hexamethylphosphoric triamide (HMPA) was added dropwise to the mixture, which was controlled to a temperature around 50° C. and matured at the temperature for 3 hours. An analysis of the contents for composition by gas chromatography proved the completion of ring-opening reaction. The yield of the synthetic intermediate, both end chloro-terminated silane compound was about 85% as measured by GC.

Next, another four-necked flask equipped with a reflux condenser, stirrer and thermometer was thoroughly purged with nitrogen and charged with 136 g of water. While cooling with ice and stirring, the ring-opening reaction liquid was added dropwise over 1 hour to the water below 10° C. After the completion of dropwise addition, the mixture was matured for 1 hour, after which the completion of hydrolysis reaction was confirmed. Then, 180 g of isooctane was fed to the reactor and the reaction mixture was washed with water by conventional means. After the water washing, the upper or organic layer was concentrated by removing isooctane under reduced pressure. By distillation under reduced pressure, 98 g of a liquid fraction having a boiling point of 123–132° C. at about 0.2 kPa was collected. The fraction collected had a purity of 98% (a mixture of several structural isomers). Its quantity corresponded to a yield of 63% relative to the norbornenylmethyldichlorosilane.

The fraction was analyzed by IR spectroscopy, gas mass spectroscopy and proton-NMR. The results are shown below. With the data, the fraction was identified to be 1-norbornenyl-3,5,7-tris(3',3',3'-trifluoropropyl)-1,3,5,7-tetramethylcyclotetrasiloxane.

Figure 3:
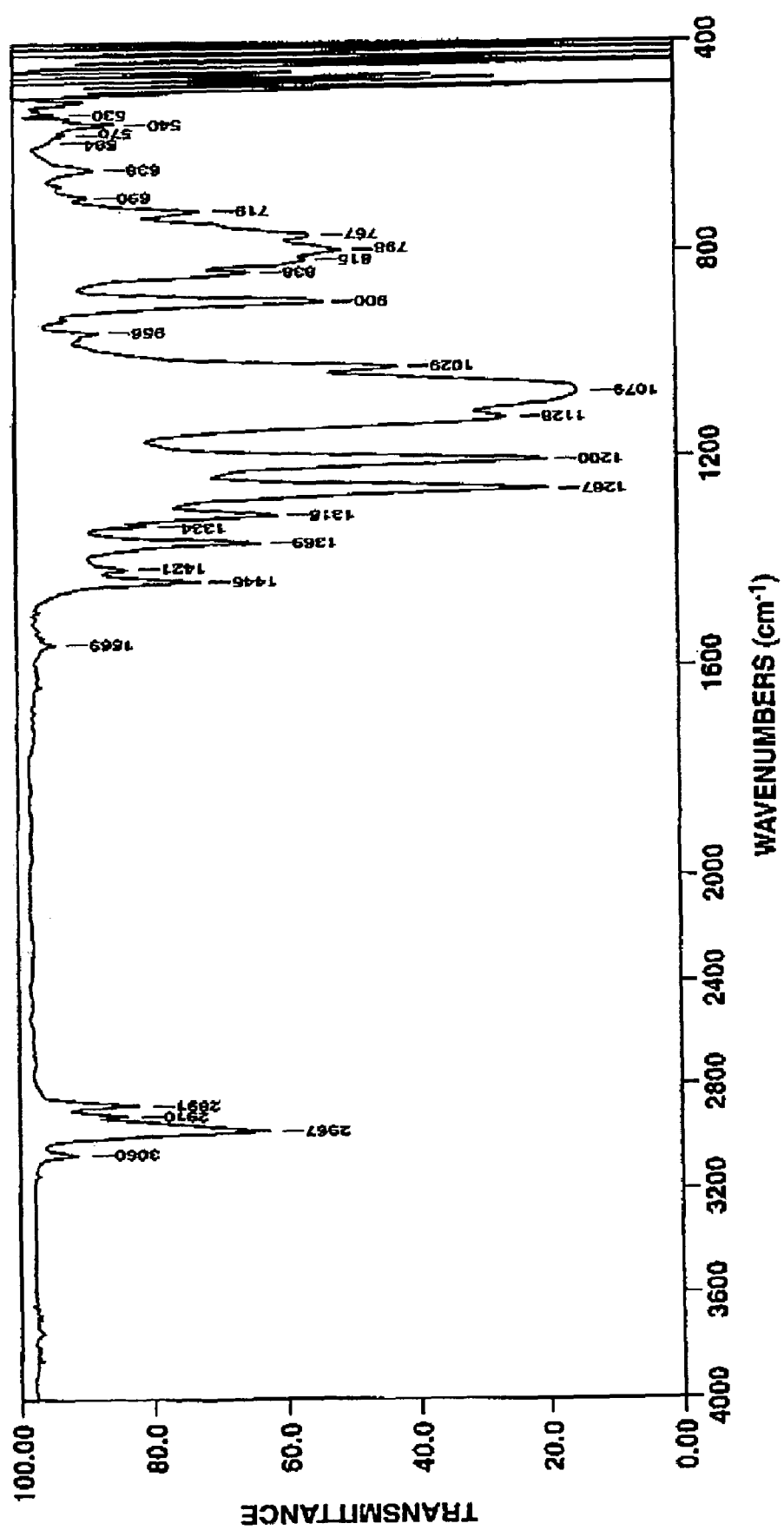
FIG. 3 is an IR spectral chart of the compound obtained in Example 3.
Figure 4:
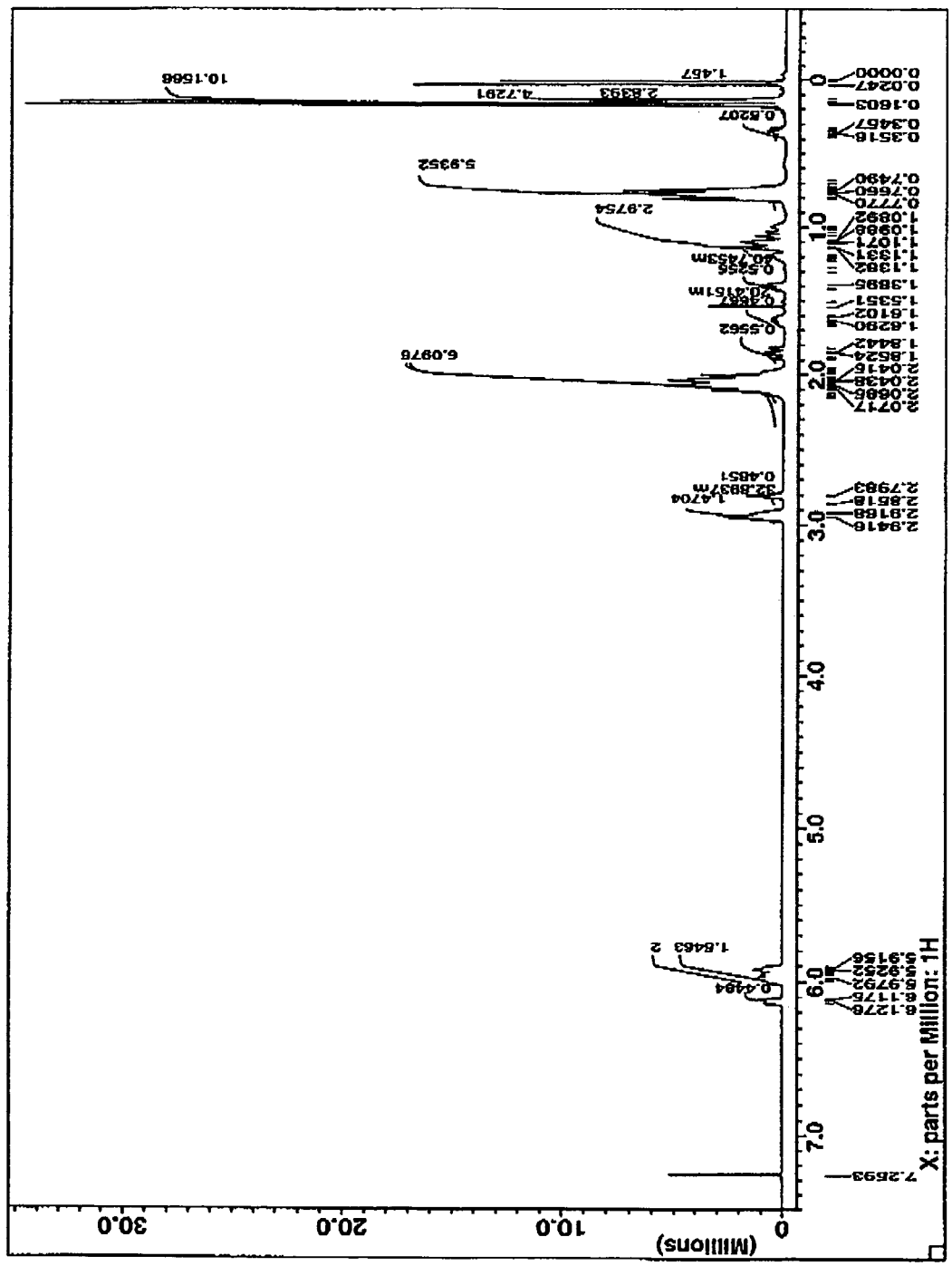
FIG. 4 is a proton-NMR spectral chart of the compound obtained in Example 3.

IR Spectra FIG. 3 Gas mass spectra molecular weight: 620 620: M⁺ 66: $C_6H_5$ NMR (proton, $CDCl_3$ solvent) FIG. 4

Japanese Patent Application Nos. 2005-146308 and 2005-174538 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A cyclic siloxane compound having the general formula (1):

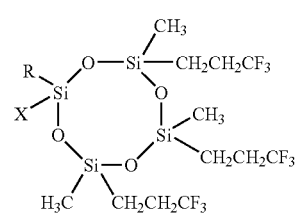

wherein X is an aliphatic unsaturation-containing organic group or cyclic unsaturation-containing organic group and R is a $C_1$–$C_6$ alkyl or phenyl.

2. The cyclic siloxane compound of claim 1 wherein X has the formula:

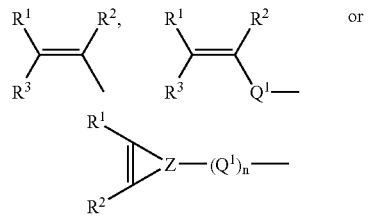

wherein $R^1$, $R^2$ and $R^3$ are each independently hydrogen, $C_1$–$C_6$ alkyl or phenyl, $Q^1$ is a divalent organic group Z is a trivalent organic group, and n is 0 or 1.

3. The cyclic siloxane compound of claim 2 wherein $Q^1$ is a linear, branched or cyclic alkylene group having 1 to 8 carbon atoms or an alkylene group which may have a branch and in which at least one methylene unit of the main chain and/or the side chain of the alkylene group may be substituted with at least one substituent group selected from the group consisting of —O—, —CO—, —COO—, —OCO—, —OCOO—, —$C_6H_4$—, —$OC_6H_4$—, —$C_6H_4O$— and —S— and the main chain of the alkylene group has 1 to 8 carbon atoms.

4. The cyclic siloxane compound of claim 2 wherein Z is a trivalent hydrocarbon group having 1 to 21 carbon atoms that forms a cyclic structure with the unsaturated bond to which $R^1$ and $R^2$ are attached or a trivalent hydrocarbon group having 2 to 21 carbon atoms in which a methylene unit of the cyclic structure is substituted with at least one substituent group selected from the group consisting of —O—, —CO—, —COO—, —OCO—, —OCOO—, —$C_6H_4$—, —$OC_6H_4$—, —$C_6H_4O$— and —S—.

5. The cyclic siloxane compound of claim 1 wherein in formula (1), R is methyl and X has the Formula:

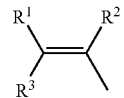

wherein $R^1$, $R^2$ and $R^3$ are each independently hydrogen or methyl.

6. The cyclic siloxane compound of claim 1 wherein in formula (1), R is methyl and X has the formula;

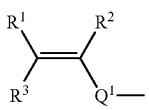

wherein R¹, R² and R³ are each independently hydrogen or methyl, and Q¹ has the formula:

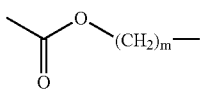

wherein m is 1 to 3.

7. The cyclic siloxane compound of claim 1 wherein in formula (1), R is methyl and X has the formula:

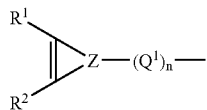

wherein R¹ and R² are each independently hydrogen or methyl, and Z—(Q¹)$_n$— has the formula:

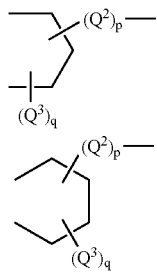

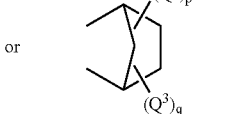

wherein Q² is —(CH$_2$)$_r$— or a group in which a methylene unit of —(CH$_2$)$_x$— is substituted with at least one substituent group selected from the group consisting of —O—, —CO—, —COO—, —OCO—, —OCOO—, —C$_6$H$_4$—, —OC$_6$H$_4$—, —C$_6$H$_4$O— and —S—, Q³ is a monovalent hydrocarbon group having 1 to 8 carbon atoms, p and q are independently 0 or 1, and r is an integer of 1 to 8.

8. A method for preparing a cyclic siloxane compound having the general formula (1), comprising the steps of reacting a dichlorosilane compound bearing an aliphatic unsaturation-containing organic group and having the general formula (2) with a fluorinated cyclic siloxane compound having the general formula (3) in the presence of a catalyst, and reacting the resulting reaction mixture with water,

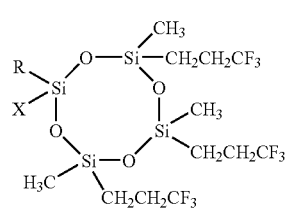 (1)

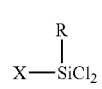 (2)

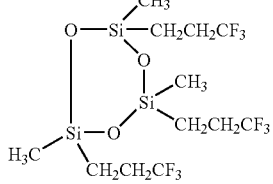 (3)

wherein X is an aliphatic unsaturation-containing organic group and R is a C$_1$–C$_6$ alkyl or phenyl.

9. The method of claim 8 wherein the catalyst is selected from the group consisting of aprotic polar solvents, quaternary ammonium salts, and quaternary phosphonium salts.

10. The method of claim 9 wherein the catalyst is an aprotic polar solvent selected from the group consisting of dimethoxyethane, dimethylformamide, hexamethylphosphoric triamide, dimethyl sulfoxide, N-methylpyrrolidone, dimethylimidazolidinone, and acetonitrile.

* * * * *